United States Patent [19]

Henkes et al.

[11] Patent Number: 4,740,646
[45] Date of Patent: Apr. 26, 1988

[54] PREPARATION OF INDANES

[75] Inventors: Erhard Henkes, Einhausen; Klaus Halbritter, Mannheim; Herbert Mayr, Gross Groenau; Wilhelm Striepe, Hof; Rudolf Pock, Erlangen, all of Fed. Rep. of Germany

[73] Assignee: BASF Aktiengesellschaft, Ludwigshafen, Fed. Rep. of Germany

[21] Appl. No.: 76,592

[22] Filed: Jul. 23, 1987

[51] Int. Cl.$^4$ .............................................. C07C 11/253
[52] U.S. Cl. ..................................... 585/409; 585/469
[58] Field of Search ................................. 585/409, 469

[56] References Cited

U.S. PATENT DOCUMENTS

| | | | |
|---|---|---|---|
| 3,246,044 | 4/1966 | Wood et al. .......................... | 585/409 |
| 3,272,883 | 9/1966 | Hughes ................................. | 585/409 |
| 3,278,622 | 10/1966 | Stofberg et al. ..................... | 585/409 |
| 4,677,238 | 6/1987 | Pedersen et al. .................... | 585/409 |

OTHER PUBLICATIONS

J. Org. Chem., vol. 48, 1159–1165 (1983).
J. Org. Chem., vol. 44, 3022–3028 (1979).
J. Chem. Research (S), 1979, pp. 184 and 185.

*Primary Examiner*—Curtis R. Davis
*Attorney, Agent, or Firm*—John H. Shurtleff

[57] ABSTRACT

Indanes are prepared by reacting substituted or unsubstituted benzyl halides with olefins in the presence of a Lewis acid as catalyst by reacting benzyl halides I

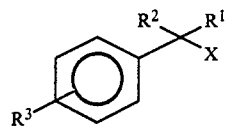

(where
$R^1$ and $R^2$=hydrogen, alkyl, alkoxy, cycloalkyl, aryl, aryloxy, aralkyl
$R^3=R^1$, halogen or an ortho-fused ring system
X=halogen)
with olefins II

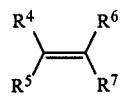

(where $R^4$ to $R^7$=hydrogen or alkyl unbranched at alpha) in the presence of catalytic amounts of titanium tetrachloride.

7 Claims, No Drawings

PREPARATION OF INDANES

The present invention relates to a process for preparing an indane by reacting a substituted or unsubstituted benzyl halide with an olefin in the presence of a Lewis acid as catalyst.

The reaction of substituted benzyl halides with olefins such as propene, isobutene and 1-methylstyrene in the presence of zinc chloride or zinc chloride etherate in dichloromethane as solvent is described in J. Org. Chem., 48 (1983), 1159-65. In general the 1:1 addition product is obtained not only at −78° C. but also at from 0° to +80° C. (see also J. Org. Chem. 29 (1964), 2685-7). The subsequent cyclization to the indane is only found when reacting 1-chloro-1-phenylethane with 1-methylstyrene at +50° C. and trityl chloride with isobutene at 0° C., in yields of 80 and 21% respectively. W. Striepe, Thesis, Erlangen University (1984), 28, 29 and 119, reveals that indanes can be obtained by first reacting p-methylcumyl chloride with an alkyl-substituted olefin at a low temperature in the presence of zinc chloride etherate and then warming the reaction mixture to room temperature in the course of 10 h. However, this method is industrially of little use because of the low temperature and a low space-time yield.

From J. Org. Chem. 44 (1979), 3022-8, and J. Chem. Res. (S) 1979, 184-5, it is known that the reaction of phenylalkyl and diphenylalkyl chlorides with phenyl-substituted alkenes such as phenylpropene and stilbene in the presence of zinc chloride in dichloromethane as solvent at 20°-40° C. leads to the corresponding indanes in yields of 70-84%. By contrast, with styrene as the olefin, the 1:1 addition product is chiefly obtained.

The disadvantages of the processes as described is the low to moderate yield of indane in some cases, the lack of choice in respect of the starting components within industrially feasible temperature ranges, and the need to carry out the reaction in the presence of a solvent, in particular in a toxicologically unsafe halogenated hydrocarbon.

It is an object of the present invention to provide a process whereby an indane is produced in a high yield and space velocity in a technically simple manner by reacting a substituted or unsubstituted benzyl halide with an olefin without an aryl substituent in the presence of a Lewis acid as catalyst.

We have found that this object is achieved with a process for preparing an indane by reacting a substituted or unsubstituted benzyl halide with an olefin in the presence of a Lewis acid as catalyst, which comprises reacting a benzyl halide of the formula I

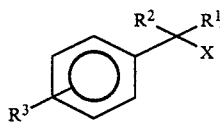

where $R^1$, $R^2$ and $R^3$ are each hydrogen, alkyl, alkoxy cycloalkyl, aryl, aryloxy or aralkyl, $R^3$ can in addition be halogen or form an ortho-fused ring system, and X is halogen, with an olefin of the formula II

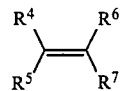

where $R^4$, $R^5$, $R^6$ and $R^7$ are each hydrogen or alkyl which is unbranched in the alpha position, in the presence of a catalytic amount of titanium tetrachloride.

The process according to the invention uses benzyl halides I, for example substituted or unsubstituted benzyl fluorides, chlorides or bromides. Benzyl fluorides are preferred because they are the most easily available. The preparation of substituted benzyl fluorides and bromides is described for example in J. Org. Chem. 29 (1964), 2685-7.

$R^1$ and $R^2$ can each be not only hydrogen but also branched or unbranched alkyl, e.g. $C_1$-$C_{12}$-alkyl, in particular $C_1$-$C_8$-alkyl, preferably $C_1$-$C_4$-alkyl, alkoxy, e.g. $C_1$-$C_8$-alkoxy, preferably $C_1$-$C_4$-alkoxy, $C_5$- or $C_6$-cycloalkyl, aryl, e.g. phenyl or phenyl with inert substituents, such as halogen-, alkyl- or alkoxy-substituted phenyl, aryloxy, e.g. phenoxy, or aralkyl e.g. $C_6$-$C_{12}$-aralkyl. Examples are methyl, ethyl, propyl, isopropyl, butyl, tert.-butyl, pentyl, hexyl, octyl, methoxy, ethoxy, cyclopentyl, cyclohexyl, phenyl, p-chlorophenyl, tolyl, phenoxy, phenylethyl and benzyl.

$R^3$ has the meanings given for $R^1$ and $R^2$ and can in addition be halogen, e.g. fluorine, chlorine or bromine, or form an ortho-fused ring system, for example by combining with the phenyl ring to form a naphthyl system.

In the olefins II, $R^4$, $R^5$, $R^6$ and $R^7$ are each hydrogen or alkyl which is unbranched in the alpha position but can otherwise be branched. Alkyl can contain for example 1 to 12, in particular 1 to 8, preferably 1 to 4, carbon atoms, examples being methyl, ethyl, propyl, butyl, 2-methylbutyl, 3,3-dimethylbutyl, pentyl, hexyl and octyl. The reaction is preferably carried out with a di-, tri- or tetra-substituted olefin, e.g. propene, but-1-ene, isobutene, pent-1-ene, hex-1-ene, but-2-ene, 2-methyl-but-2-ene, 3-methylpent-2-ene, 3,5-dimethylhex2-ene or tetramethylethylene.

In general it is possible to use 1.5 to 4, advantageously from 2 to 3, in particular from 2 to 2.5, moles of olefin per mole of benzyl halide I. A lower, for example an equimolar, amount of the olefin is possible but not expedient, since the hydrogen halide formed in the course of the reaction may become bonded to the olefin and thereby be consumed. On the other hand, the excess amount of olefin can be higher than specified above, but in general this offers no further benefit.

The reaction is carried out according to the invention in the presence of a catalytic amount of titanium tetrachloride, since this catalyst particularly favors the ring closure reaction which gives the indane. The amount of catalyst ranges expediently from 0.002 to 0.2, in particular from 0.004 to 0.04, preferably from 0.01 to 0.03, mole per mole of benzyl halide I. If the amount of catalyst is higher or lower, the formation of by-products generally increases.

The reaction can be carried out in the presence or absence of solvent. Suitable solvents are those which are customary for Friedel-Crafts reactions, such as aromatic or aliphatic hydrocarbons, ethers or halogenated hydrocarbons, e.g. benzene, toluene, hexane, diethyl ether, dichloromethane, chloroform or chlorobenzene. In most cases no solvent need be present, which is a particular feature of the process according to the invention.

The reaction temperature depends on the reactivity of the starting materials, ranging in general from about −20° to +40° C. Lower temperatures are possible but in general not necessary. The process can be carried out in a conventional manner batchwise or continuously under superatmospheric pressure, reduced pressure or advantageously under atmospheric pressure using the customary techniques.

For example, it is possible to introduce the olefin first, at the reaction temperature, together with titanium tetrachloride and to add the benzyl halide I. The reaction mixture obtained is worked up in a conventional manner, for example by destroying the catalyst by adding water and distilling off excess olefin and volatile byproducts, leaving behind a residue containing indane, which can be purified, for example by distillation or recrystallization, or be used directly as it is.

Using the process according to the invention, it is possible to obtain substituted or unsubstituted indanes, in particular polyalkyl-substituted indanes, in high yields in a technically simple manner. The products, which are of interest for use as intermediates in the production of, for example, scents, are frequently obtained in sufficient purity for direct use without distillative purification. The preparation of bicyclic aromatic musk scents such as galaxolid from the indanes obtainable according to the invention is described for example in EP No. 89,207 or U.S. Pat. Nos. 4,265,818 and 4,315,951.

EXAMPLE 1

Preparation of 1,1,2,3,3-pentamethylindane 1,750 g (25 mol) of 2-methylbut-2-ene were introduced first, together with 32 g (0.17 mol) of titanium tetrachloride at −5° C., and 1,547 g (10 mol) of 2-chloro2-phenylpropane (cumyl chloride) were added in the course of 3 hours during which the temperature did not rise above +10° C. After 1 h of stirring at room temperature, the reaction mixture was worked up in a conventional manner by adding 12.3 g (0.68 mol) of water, stirring at room temperature and, after phase separation, distilling the excess olefin and the tert.-amyl chloride obtained as a by-product out of the organic phase.

This left 1,851 g of residue which, according to gas chromatography, contained 94% by weight of 1,1,2,3,3-pentamethylindane, corresponding to a yield of 92.5%, based on cumyl chloride, and was directly usable for subsequent reactions.

When the same reaction was carried out in the presence of only 8 g (0.042 mol) of titanium tetrachloride, the product was obtained, after distillative purification, in a yield of 80.3%, based on cumyl chloride.

COMPARATIVE EXAMPLE 1

(a) 87.5 (1.25 mol) of 2-methylbut-2-ene were introduced first, together with 1.19 g (8.5 mmol) of anhydrous zinc chloride in 0.38 g (5.1 mmol) of diethyl ether at 0° C., and at that temperature 78 g (0.5 mol) of cumyl chloride were added in the course of 1 hour. This was followed by stirring at room temperature for 1 hour.

A customary workup with distillative removal of volatiles left a residue of 75.7 g which, according to gas chromatography, contained 11% by weight of 1,1,2,3,3-pentamethylindane, corresponding to a yield of 8.9%, based on cumyl chloride.

(b) The same reaction as in a) but in the presence of 132 ml of methylene chloride gave 50.9% of 1,1,2,3,3-pentamethylindane, based on cumyl chloride (determined by gas chromatography).

EXAMPLE 2

Preparation of 1,1,2,2,3,3-hexamethylindane 110 g (1.31 mol) of tetramethylethylene and 82.8 g (0.535 mol) of cumyl chloride were dissolved in 1.6 l of methylene chloride and cooled down to −75° C. 10 ml of titanium tetrachloride were added in the course of 10 min, and the reaction mixture was stirred at −75° C. for 1 h. The solution was subsequently poured onto 900 ml of dilute hydrochloric acid, and the organic phase was separated off and dried. After the drying agent had been filtered off and volatiles been separated off, the residue was distilled. Yield: 78.2 g ( ≐72% of theory) of 1,1,2,2,3,3-hexamethylindane, boiling point 52°–55° C./0.5 mbar. $^1$H-NMR (CCl$_4$): δ=0.85 (s, 6H), 1.17 (12H), 7.00 (s, 4H).

We claim:

1. A process for preparing an indane by reacting a substituted or unsubstituted benzyl halide with an olefin in the presence of a Lewis acid as catalyst, which comprises reacting a benzyl halide of the formula I

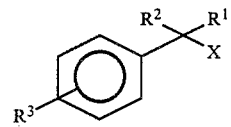

where $R^1$, $R^2$ and $R^3$ are each hydrogen or alkyl, alkoxy, cycloalkyl, aryl, aryloxy or aralkyl, $R^3$ can in addition be halogen or form an ortho-fused ring system, and X is halogen, with an olefin of the formula II

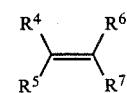

where $R^4$, $R^5$, $R^6$ and $R^7$ are each hydrogen or alkyl which is unbranched in the alpha position, in the presence of a catalytic amount of titanium tetrachloride.

2. A process as claimed in claim 1, wherein a benzyl chloride or bromide is reacted.

3. A process as claimed in claim 1, wherein from 2 to 3 moles of olefin II are used per mole of benzyl halide I.

4. A process as claimed in claim 1, wherein from 0.004 to 0.04 mole of titanium tetrachloride is used per mole of benzyl halide I.

5. A process as claimed in claim 1, wherein from 0.01 to 0.03 mole of titanium tetrachloride is used per mole of benzyl halide I.

6. A process as claimed in claim 1, wherein the reaction is carried out in the absence of a solvent.

7. A process as claimed in claim 1, wherein the reaction is carried out at from −20° to +40° C.

* * * * *